United States Patent

Soma et al.

(10) Patent No.: US 8,076,402 B2
(45) Date of Patent: Dec. 13, 2011

(54) BISPHENOL MONOESTER COMPOUND

(75) Inventors: Ryoji Soma, Nara (JP); Toyomochi Tamato, Nishinomiya (JP); Masatsugu Akiba, Toyonaka (JP); Tatsumi Nuno, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 409 days.

(21) Appl. No.: 12/292,797

(22) Filed: Nov. 26, 2008

(65) Prior Publication Data

US 2009/0143517 A1 Jun. 4, 2009

(30) Foreign Application Priority Data

Nov. 29, 2007 (JP) .................. 2007-308502

(51) Int. Cl.
- C08K 5/105 (2006.01)
- C08K 5/134 (2006.01)
- C08K 5/11 (2006.01)
- C07C 39/21 (2006.01)
- C07C 69/773 (2006.01)
- C07C 69/618 (2006.01)
- C07C 69/73 (2006.01)
- C07C 69/76 (2006.01)

(52) U.S. Cl. ........ 524/291; 524/294; 524/299; 524/349; 560/130; 560/140; 560/183; 560/225

(58) Field of Classification Search ............... 524/291, 524/294, 299, 349; 560/130, 140, 183, 225
See application file for complete search history.

(56) References Cited

U.S. PATENT DOCUMENTS

| | | | |
|---|---|---|---|
| 5,128,398 A | | 7/1992 | Sasaki et al. |
| 5,281,646 A | * | 1/1994 | Yachigo et al. ............... 524/291 |
| 5,981,638 A | * | 11/1999 | Ida et al. ..................... 524/291 |
| 6,103,794 A | * | 8/2000 | Laver ........................... 524/84 |

FOREIGN PATENT DOCUMENTS

| | | |
|---|---|---|
| EP | 0 322 166 | 6/1989 |
| JP | 2006176419 A | * 7/2006 |

OTHER PUBLICATIONS

European Search Report dated Feb. 24, 2009 in European Patent Application No. 08 16 9878 corresponding to the present application.

* cited by examiner

*Primary Examiner* — Michael Pepitone
(74) *Attorney, Agent, or Firm* — Wenderoth, Lind & Ponack, L.L.P.

(57) ABSTRACT

A bisphenol monoester compound represented by the formula (1):

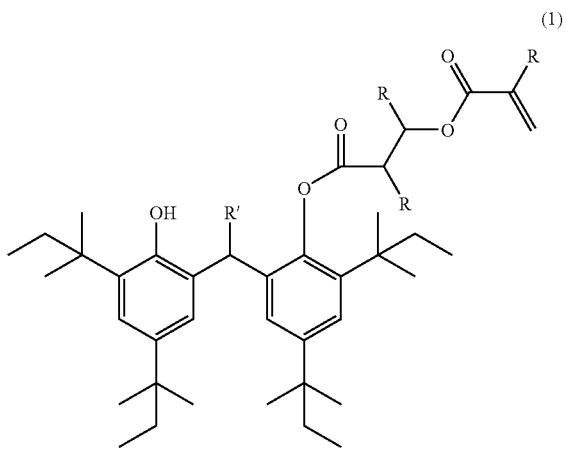

(in the formula (1), Rs each represent independently a hydrogen atom or a methyl group, and R' represents an alkyl group of a carbon number of 1 to 6, or a hydrogen atom).

8 Claims, No Drawings

BISPHENOL MONOESTER COMPOUND

TECHNICAL FIELD

The present invention relates to a bisphenol monoester compound.

BACKGROUND ART

In order to improve thermal stability of a thermoplastic polymer, a stabilizer containing a compound represented by the formula (I) as an active component is disclosed in Patent Literature 1.

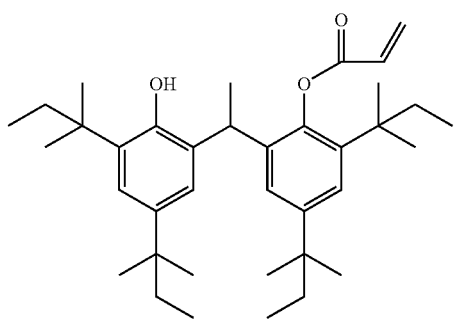
(I)

Patent Literature: 1 JP-A No. 1-168643

DISCLOSURE OF THE INVENTION

An object of the present invention is to provide a compound for further improving thermal stability of a thermoplastic polymer.

Under such the circumstances, the present inventors found out a certain bisphenol monoester compound, resulting in completion of the present invention. That is, the present invention provides the following [1] to [6].

[1] A bisphenol monoester compound represented by the formula (I).

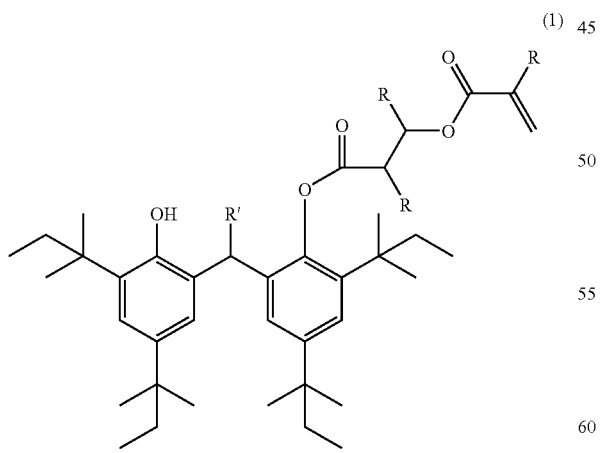
(1)

(In the formula (I), Rs each represent independently a hydrogen atom or a methyl group, and R' represents an alkyl group of a carbon number of 1 to 6 or a hydrogen atom)

[2] A stabilizer comprising the bisphenol monoester compound as defined in [1] as an active component.

[3] The stabilizer according to [2], comprising 0.005 to 100% by weight of the bisphenol monoester compound as defined in [1].

[4] A thermoplastic polymer composition comprising the stabilizer as defined in [2] or [3], and a thermoplastic polymer.

[5] Use of the stabilizer as defined in [2] or [3] for thermally stabilizing a thermoplastic polymer.

[6] A process for producing the bisphenol monoester compound as defined in [1], comprising reacting bisphenol represented by the formula (2):

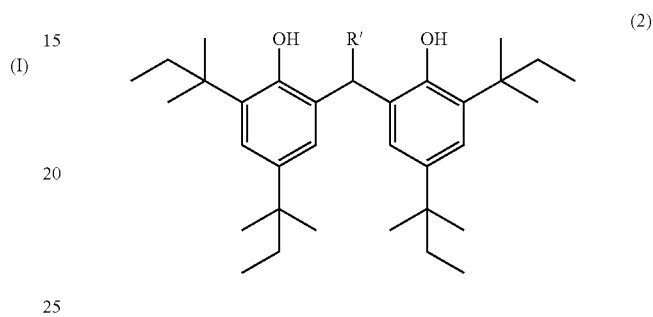
(2)

(in the formula (2), R' represents an alkyl group of a carbon number of 1 to 6 or a hydrogen atom) with a compound represented by the formula (3):

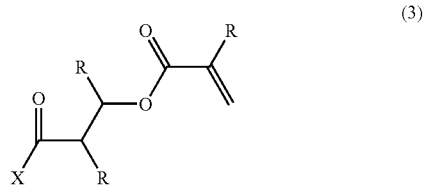
(3)

(in the formula (3), Rs each represent independently a hydrogen atom or a methyl group, and X represents a halogen atom, a hydroxy group or an alkoxy group of a carbon number of 1 to 6).

MODE FOR CARRYING OUT THE INVENTION

The compound of the present invention is a bisphenol monoester compound represented by the formula (1) (hereinafter, referred to as Compound (1) in some cases).

Herein, Rs each represent independently a hydrogen atom or a methyl group. Preferably, all of Rs are a hydrogen atom.

R' is an alkyl group of a carbon atom of 1 to 6 such as a methyl group, an ethyl group and a n-butyl group, or a hydrogen atom, particularly preferably a methyl group.

Examples of a process for producing Compound (1) include a process for reacting 2,4-di-tert-pentylphenol and R'CHO to produce bisphenol (2) and, then, reacting the bisphenol (2) with a compound represented by the formula (3) (hereinafter, referred to as Compound (3) in some cases). Particularly, X of Compound (3) is preferably a halogen atom such as chlorine. Specifically, a compound in which X of Compound (3) is a hydroxy group is converted into halide with thionyl chloride, and the halide may be reacted with the bisphenol.

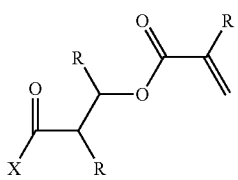

(3)

(In the formula (3), Rs each represent independently a hydrogen atom or a methyl group, and X represents a halogen atom, a hydroxy group or an alkoxy group of a carbon number of 1 to 6).

Examples of Compound (3) include 2-carboxyethyl acrylate, 2-carboxyethyl methacrylate, 2-carboxy-2-methyl methacrylate, 2-carboxy-2-methyl acrylate, and chloride thereof.

2-Carboxyethyl acrylate is commercially available, for example, from Aldrich.

The stabilizer of the present invention is preferably a thermal stabilizer for thermally stabilizing a thermoplastic polymer. The stabilizer of the present invention is a stabilizer containing Compound (1) as an active component, and contains the Compound (1) at 0.005 to 100% by weight, preferably 0.01 to 100% by weight, further preferably 0.1 to 100% by weight.

The stabilizer of the present invention may contain an additive other than Compound (1) in such a range that the effect of the present invention is not inhibited. Examples of such the additive include antioxidants such as phenol-based antioxidants, phosphorus-based antioxidants and sulfur-based antioxidants, ultraviolet absorbing agents, light stabilizers, metal inactivating agents, nucleating agents, lubricants, antistatic agents, flame-retardants, fillers, pigments, plasticizes, anti-blocking agents, surfactants, processing aids, expanding agents, emulsifiers, gloss agents, neutralizing agents such as calcium stearate and hydrotalcite, and binders.

Particularly, antioxidants are preferable and, among others, a phenol-based antioxidant is preferable.

Examples of the phenol-based antioxidant include alkylated monophenols such as 2,6-di-t-butyl-4-methylphenol, 2,4,6-tri-t-butylphenol, 2,6-di-t-butylphenol, 2-t-butyl-4,6-dimethylphenol, 2,6-di-t-butyl-4-ethylphenol, 2,6-di-t-butyl-4-n-butylphenol, 2,6-di-t-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-t-butyl-4-methoxymethylphenol, 2,6-di-nonyl-4-methylphenol, 2,4-dimethyl-6-(1'-methylundecyl-1'-yl)phenol, 2,4-dimethyl-6-(1'-methylheptadecyl-1'-yl)phenol, 2,4-dimethyl-6-(1'-methyltridecyl-1'-yl)phenol, and a mixture thereof, alkylthiomethylphenols such as 2,4-dioctylthiomethyl-6-t-butylphenol, 2,4-dioctylthiomethyl-6-methylphenol, 2,4-dioctylthiomethyl-6-ethylphenol, 2,6-didodecylthiomethyl-4-nonylphenol, and a mixture thereof, hydroquionchydroquinones and alkylated hydroquinones such as 2,6-di-t-butyl-4-methoxyphenol, 2,5-di-t-butylhydroquione, 2,5-di-t-amylhydroquione, 2,6-diphenyl-4-octadecyloxyphenol, 2,6-di-t-butylhydroquione, 2,5-di-t-butyl-4-hydroxyanisole, 3,5-di-t-butyl-4-hydroxyphenyl stearate, bis(3,5-di-t-butyl-4-hydroxyphenyl) adipate, and a mixture thereof, tocopherols such as α-tocopherol, β-tocopherol, γ-tocopherol, δ-tocopherol, and a mixture thereof, hydroxylated thiodiphenyl ethers such as 2,2'-thiobis(6-t-butylphenol), 2,2'-thiobis(4-methyl-6-t-butylphenol), 2,2'-thiobis(4-octylphenol), 4,4'-thiobis(3-methyl-6-t-butylphenol), 4,4'-thiobis(2-methyl-6-t-butylphenol), 4,4'-thiobis(3,6-di-t-amylphenol), and 4,4'-(2,6-dimethyl-4-hydroxyphenyl) disulfide, alkylidenebisphenols such as 2,2'-methylenebis(4-methyl-6-t-butylphenol), 2,2'-methylenebis(4-ethyl-6-t-butylphenol), 2,2'-methylenebis[4-methyl-6-(α-methylcyclohexyl) phenol)], 2,2'-methylenebis(4-methyl-6-cyclohexylphenol), 2,2'-methylenebis(4-methyl-6-nonylphenol), 2,2'-methylenebis(4,6-di-t-butylphenol), 2,2'-ethylidenebis(4,6-di-t-butylphenol), 2,2'-ethylidenebis(4-isobutyl-6-t-butylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(6-t-butyl-2-methylphenol), 4,4'-methylenebis(2,6-di-t-butylphenol), 4,4'-butylidenebis(3-methyl-6-t-butylphenol), 1,1-bis(4-hydroxyphenyl) cyclohexane, 1,1-bis(5-t-butyl-4-hydroxy-2-methylphenyl)butane, 2,6-bis(3-t-butyl-5-methyl-2-hydroxybenzyl)-4-methylphenol, 1,1,3-tris(5-t-butyl-4-hydroxy-2-methylphenyl)butane, 1,1-bis(5-t-butyl-4-hydroxy-2-methylphenyl)-3-n-dodecylmercaptobutane, ethylene glycol bis[3,3-bis-3'-t-butyl-4'-hydroxyphenyl) butyrate], bis(3-t-butyl-4-hydroxy-5-methylphenyl)dicyclopentadiene, bis[2-(3'-t-butyl-2'-hydroxy-5'-methylbenzyl)-6-t-butyl-4-methylphenyl]terephthalate, 1,1-bis(3,5-dimethyl-2-hydroxyphenyl)butane, 2,2-bis(3,5-di-t-butyl-4-hydroxyphenyl)propane, 2,2-bis(5-t-butyl-4-hydroxy-2-methylphenyl)-4-n-dodecylmercaptobutane, 1,1,5,5-tetra(5-t-butyl-4-hydroxy-2-methylphenyl)pentane, 2-t-butyl-6-(3'-t-butyl-5'-methyl-2'-hydroxybenzyl)-4-methylphenyl acrylate, 2,4-di-t-pentyl-6-[1-(2-hydroxy-3,5-di-t-pentylphenyl)ethyl]phenyl acrylate, and a mixture thereof, and a derivative thereof, O-benzyl derivatives, N-benzyl derivatives and S-benzyl derivatives such as 3,5,3',5'-tetra-t-butyl-4,4'-dihydroxydibenzyl ether, octadecyl-4-hydroxy-3,5-dimethylbenzyl mercaptoacetate, tris(3,5-di-t-butyl-4-hydroxybenzyl) amine, bis(4-t-butyl-3-hydroxy-2,6-dimethylbenzyl) dithioterephthalate, bis(3,5-di-t-butyl-4-hydroxybenzyl) sulfide, isooctyl-3,5-di-t-butyl-4-hydroxybenzyl mercaptoacetate, and a mixture thereof, hydroxybenzylated malonate derivatives such as dioctadecyl-2,2-bis(3,5-di-t-butyl-2-hydroxybenzyl)malonate, dioctadecyl-2-(3-t-butyl-4-hydroxy-5-methylbenzyl) malonate, didodecylthioethyl-2,2-bis(3,5-di-t-butyl-4-hydroxybenzyl) malonate, bis[4-(1,1,3,3-tetramethylbutyl)phenyl]-2,2-bis (3,5-di-t-butyl-4-hydroxybenzyl) malonate, and a mixture thereof, aromatic hydroxybenzyl derivatives such as 1,3,5-trimethyl-2,4,6-tris(3,5-di-t-butyl-4-hydroxybenzyl) benzene, 1,4-bis(3,5-di-t-butyl-4-hydroxybenzyl)-2,3,5,6-tetramethylbenzene, 2,4,6-tris(3,5- di-t-butyl-4-hydroxybenzyl) phenol, and a mixture thereof, triazine derivatives such as 2,4-bis(n-octylthio)-6-(4-hydroxy-3,5-di-t-butylanilino)-1,3,5-triazine, 2-n-octylthio-4,6-bis(4-hydroxy-3,5-di-t-butylanilino)-1,3,5-triazine, 2-n-octylthio-4,6-bis(4-hydroxy-3,5-di-t-butylphenoxy)-1,3,5-triazine, 2,4,6-tris(3,5-di-t-butyl-4-phenoxy)-1,3,5-triazine, tris(4-t-butyl-3-hydroxy-2,6-dimethylbenzyl)isocyanurate, tris(3,5-di-t-butyl-4-hydroxybenzyl) isocyanurate, 2,4,6-tris(3,5-di-t-butyl-4-hydroxyphenylethyl)-1,3,5-triazine, 2,4,6-tris(3,5-di-t-butyl-4-hydroxyphenylpropyl)-1,3,5-triazine, tris(3,5-dicyclohexyl-4-hydroxybenzyl) isocyanurate, tris[2-(3',5'-di-t-butyl-4'-hydroxycinnamoyloxy)ethyl]isocyanurate, and a mixture thereof, benzylphosphonate derivatives such as dimethyl-3,5-di-t-butyl-4-hydroxybenzylphosphonate, diethyl-3,5-di-t-butyl-4-hydroxybenzylphosphonate, dioctadecyl-3,5-di-t-butyl-4-hydroxybenzylphosphonate, dioctadecyl-5-t-butyl-4-hydroxy-3-methylbenzylphosphonate, 3,5-di-t-butyl-4-hydroxybenzylphosphonic acid monoester potassium salt, and a mixture thereof, acylaminophenol derivatives such as 4-hydroxylauric acid anilide, 4-hydroxystearic acid anilide, octyl-N-(3,5-di-t-butyl-4-hydroxyphenyl)carbamate and, a mixture thereof, esters of β-(3,5-di-t-butyl-4-hydroxyphenyl)propionic acid, with a monohydric alcohol or a polyhydric alcohol such as methanol, ethanol, octanol, octadecanol, ethylene glycol, 1,3-propanediol, 1,4-butanediol, 1,6-hexanediol, 1,9-nonanediol, neopentyl glycol, diethylene glycol, thioethylene glycol, spiro glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2,2,2]octane, and a mixture thereof, esters of β-(5-t-butyl-4-hydroxy-3-methylphenyl)propionic acid, with a monohydric alcohol or a polyhydric alcohol such as methanol, ethanol, octanol, octadecanol, ethylene glycol, 1,3-propanediol, 1,4-butanediol, 1,6-hexanediol, 1,9-nonanediol, neopentyl glycol, diethylene glycol, thioethylene glycol, spiro glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2,2,2]octane and a mixture thereof, esters of β-(3,5-dicyclohexyl-4-hydroxyphenyl)propionic acid, with a monohydric alcohol or a polyhydric alcohol such as methanol, ethanol, octanol, octadecanol, ethylene glycol, 1,3-propanediol, 1,4-butanediol, 1,6-hexanediol, 1,9-nonanediol, neopentyl glycol, diethylene glycol, thioethylene glycol, spiro glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2,2,2]octane and a mixture thereof, esters of 3,5-di-t-butyl-4-hydroxyphenylacetic acid, with a monohydric alcohol or a polyhydric alcohol such as methanol, ethanol, octanol, octadecanol, ethylene glycol, 1,3-propanediol, 1,4-butanediol, 1,6-hexanediol, 1,9-nonanediol, neopentyl glycol, diethylene glycol, thioethylene glycol, Spiro glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2,2,2] octane and a mixture thereof, amides of β-(3,5-di-t-butyl-4-hydroxyphenyl)propionic acid such as N,N'-bis[3-(3',5'-di-t-butyl-4'-hydroxyphenyl)propionyl]hydrazine, N,N'-bis[3-(3',5'-di-t-butyl-4'-hydroxyphenyl)propionyl]hexamethylenediamine, N,N'-bis[3-(3',5'-di-t-butyl-4'-hydroxyphenyl)propionyl] trimethylenediamine, and a mixture thereof. Such the phenol-based antioxidants may be used alone, or may be used by mixing two or more kinds.

Examples of a particularly preferable phenol-based antioxidant include 2,6-di-t-butyl-4-methylphenol, 2,4,6-tri-t-butylphenol, 2,4-dioctylthiomethyl-6-methylphenol, 2,2'-thiobis(6-t-butylphenol), 4,4'-thiobis(3-methyl-6-t-butylphenol), 2,2'-methylenebis(4-methyl-6-t-butylphenol), 2,2'-methylenebis(4-ethyl-6-t-butylphenol), 2,2'-methylenebis[4-methyl-6-(α-methylcyclohexyl)phenol], 2,2'-methylenebis(4-methyl-6-cyclohexylphenol), 2,2'-methylenebis(4,6-di-t-butylphenol), 2,2'-ethylidenebis(4,6-di-t-butylphenol), 4,4'-methylenebis(6-t-butyl-2-methylphenol), 4,4'-methylenebis(2,6-di-t-butylphenol), 4,4'-butylidenebis(3-methyl-6-t-butylphenol), 1,1-bis(4-hydroxyphenyl)cyclohexane, 1,1-bis(5-t-butyl-4-hydroxy-2-methylphenyl)butane, 1,1,3-tris(5-t-butyl-4-hydroxy-2-methylphenyl)butane, ethylene glycol bis[3,3-bis-3'-t-butyl-4'-hydroxyphenyl]butyrate], 2,4,6-tris(3,5-di-t-butyl-4-phenoxy)-1,3,5-triazine, tris(4-t-butyl-3-hydroxy-2,6-dimethylbenzyl)isocyanurate, bis(3,5-di-t-butyl-4-hydroxybenzyl)isocyanurate, tris[2-(3',5'-di-t-butyl-4'-hydroxycinnamoyloxy)ethyl]isocyanurate, diethyl-3,5-di-t-butyl-4-hydroxybenzyl phosphonate, di-n-octadecyl-3,5-di-t-butyl-4-hydroxybenzyl phosphonate, 3,5-di-t-butyl-4-hydroxybenzyl phosphonic acid monoester calcium salt, n-octadecyl 3-(3,5-di-t-butyl-4-hydroxyphenyl)propionate, neopentane tetrayltetrakis(3,5-di-t-butyl-4-hydroxycinnamate), thiodiethylenebis(3,5-di-t-butyl-4-hydroxycinnamate), 1,3,5-trimethyl-2,4,6-tris(3,5-di-t-butyl-4-hydroxybenzyl)benzene, 3,6-dioxaoctamethylenebis(3,5-di-t-butyl-4-hydroxycinnamate), hexamethylenebis(3,5-di-t-butyl-4-hydroxycinnamate), triethylene glycol bis(5-t-butyl-4-hydroxy-3-methylcinnamate), 3,9-bis[2-(3-(3-t-butyl-4-hydroxy-5-methylphenyl)propionyloxy)-1,1-dimethylethyl]-2,4,8,10-tetraoxaspiro[5·5]undecane, N,N'-bis[3-(3',5'-di-t-butyl-4'-hydroxyphenyl)propionyl] hydrazine, N,N'-bis[3-(3',5'-di-t-butyl-4'-hydroxyphenyl)propionyl]hexamethylenediamine, 2-t-butyl-6-(3'-t-butyl-5'-methyl-2'-hydroxybenzyl)-4-methylphenyl acrylate, 2,4-di-t-pentyl-6-[1-(2-hydroxy-3,5-di-t-pentylphenyl)ethyl]phenyl acrylate, and a mixture thereof, and these may be used alone, two or more kinds may be used.

Inter alia, 2-t-butyl-6-(3'-t-butyl-5'-methyl-2'-hydroxybenzyl)-4-methylphenyl acrylate, 2,4-di-t-pentyl-6-[1-(2-hydroxy-3,5-di-t-pentylphenyl)ethyl]phenyl acrylate, and a mixture thereof are particularly preferable.

The composition of the present invention is a thermoplastic polymer composition containing the stabilizer, and a thermoplastic polymer.

Examples of the thermoplastic polymer include polypropylene-based resins such as an ethylene-propylene copolymer, polyethylene-based resins (high density polyethylene (HD-PE), low density polyethylene (LD-PE), straight low-density polyethylene (LLDPE) etc.), a methylpentene polymer, an ethylene-ethyl acrylate copolymer, an ethylene-vinyl acetate copolymer, polystyrenes (polystyrene such as poly(p-methylstyrene), poly(α-methylstyrene), an acrylonitrile-styrene copolymer, an acrylonitrile-butadiene-styrene copolymer, a special acryl rubber-acrylonitrile-styrene copolymer, an acrylonitrile-chlorinated polyethylene-styrene copolymer, a styrene-butadiene copolymer etc.), chlorinated polyethylene, polychloroprene, a chlorinated rubber, polyvinyl chloride, polyvinylidene chloride, a methacryl resin, an ethylene-vinyl alcohol copolymer, a fluorine resin, polyacetal, a grafted polyphenylene ether resin, a polyphenylene sulfide resin, polyurethane, polyamide, polyester resins (e.g. polyethylene terephthalate, polybutylene terephtalate etc.), polycarbonate, polyacrylate, polysulfone, polyether ether ketone, polyether sulfone, an aromatic polyester resin, a diallyl phthalate prepolymer, a silicone resin, 1,2-polybutadiene, polyisoprene, a butadiene/acrylonitrile copolymer, and an ethylene-methyl methacrylate copolymer. Particularly, from a viewpoint of good processibility, a polyethylene-based resin, a polypropylene-based resin, and polystyrenes are preferable and, among others, a polypropylene-based resin, an acrylonitrile-butadiene-styrene copolymer, and a styrene-butadiene copolymer are preferable.

Herein, the polypropylene-based resin means polyolefin containing a structural unit derived from propylene and, specifically, examples include a crystalline propylene homopolymer, a propylene-ethylene random copolymer, a propylene-$\alpha$-olefin random copolymer, a propylene-ethylene-$\alpha$-olefin copolymer, and a propylene-based block copolymer consisting of a propylene homopolymer component or a copolymer component mainly consisting of propylene, and a copolymer component of propylene, ethylene and/or $\alpha$-olefin.

When the polypropylene-based resin is used as the thermoplastic polymer in the present invention, one kind of the polypropylene-based resin may be used, or two or more kinds of polypropylene-based resins may be used by blending them.

The $\alpha$-olefin is usually $\alpha$-olefin of a carbon atom number of 4 to 12, and examples include 1-butene, 1-pentene, 1-hexene, 4-methyl-1-pentene, 1-octene, and 1-decene, further preferably 1-butene, 1-hexene and 1-octene.

Examples of the propylene-$\alpha$-olefin random copolymer include a propylene-1-butene random copolymer, a propylene-1-hexene random copolymer, and a propylene-1-octene random copolymer.

Examples of the propylene-ethylene-$\alpha$-olefin copolymer include a propylene-ethylene-1-butene copolymer, a propylene-ethylene-1-hexene copolymer, and a propylene-ethylene-1-octene copolymer.

Examples of the copolymer component consisting mainly consisting of propylene in the polypropylene-based block copolymer consisting of a propylene homopolymer component or a copolymer component mainly consisting of propylene, and a copolymer component of propylene, ethylene and/or $\alpha$-olefin include a propylene-ethylene copolymer component, a propylene-1-butene copolymer component, and a propylene-1-hexene copolymer component, examples of the copolymer component of propylene, ethylene and/or $\alpha$-olefin include a propylene-ethylene copolymer component, a propylene-ethylene-1-butene-copolymer component, a propylene-ethylene-1-hexene copolymer component, a propylene-ethylene-1-octene component, a propylene-1-butene copolymer component, a propylene-1-hexene copolymer component, and a propylene-1-octone copolymer component. A content of ethylene and/or $\alpha$-olefin of a carbon number of 4 to 12 in the copolymer component of propylene, ethylene and/or $\alpha$-olefin is usually 0.01 to 20% by weight.

In addition, examples of the polypropylene-based block copolymer consisting of a propylene homopolymer component or a copolymer component mainly consisting of propylene, and a copolymer component of propylene, ethylene and/or $\alpha$-olefin include a propylene-ethylene block copolymer, a (propylene)-(propylene-ethylene) block copolymer, a (propylene)-(propylene-ethylene-1-butene) block copolymer, a (propylene)-(propylene-ethylene-1-hexene) block copolymer, a (propylene)-(propylene-1-butene) block copolymer, a (propylene)-(propylene-1-hexene) block copolymer, a (propylene-ethylene)-(propylene-ethylene-1-butene) block copolymer, a (propylene-ethylene)-(propylene-ethylene-1-hexene) block copolymer, a (propylene-ethylene)-(propylene-1-butene) block copolymer, a (propylene-ethylene)-(propylene-1-hexene) block copolymer, a (propylene-1-butene)-(propylene-ethylene) block copolymer, a (propylene-1-butene)-(propylene-ethylene-1-butene) block copolymer, a (propylene-1-butene)-(propylene-ethylene-1-hexene) block copolymer, a (propylene-1-butene)-(propylene-1-butene) block copolymer, and a (propylene-1-butene)-(propylene-1-hexene) block copolymer.

When the polypropylene-based resin is used as the thermoplastic polymer in the present invention, the resin is preferably a crystalline propylene homopolymer, or a polypropylene-based block copolymer consisting of a propylene homopolymer component or a copolymer component mainly consisting of propylene, and a copolymer component of propylene, ethylene and/or $\alpha$-olefin of a carbon atom number of 4 to 12. Further preferable is a polypropylene-based block copolymer consisting of a propylene homopolymer component or a copolymer component mainly consisting of propylene, and a copolymer component of propylene, ethylene and/or $\alpha$-olefin of a carbon atom number of 4 to 12.

It is enough that the thermoplastic polymer composition of the present invention usually contains the stabilizer of the present invention at 5 parts by weight or less based on 100 parts by weight of the thermoplastic polymer, specifically, the composition contains the stabilizer at 0.0001 part by weight or more and 5 parts by weight or less, preferably 0.0005 part by weight or more and 3 parts by weight or less. When the amount of the stabilizer is 5 parts by weight or less, so-called bleeding phenomenon in which the stabilizer appears on a surface of the thermoplastic polymer composition tends to be suppressed, being preferable.

A process for producing the thermoplastic polymer composition of the present invention include a process of dry-blending a thermoplastic polymer and a stabilizer, melt-kneading the blend with a monoaxial or multiaxial extruder, and extrusion-molding this to obtain a pellet-like thermoplastic polymer composition, and a process of mixing a solution in which the stabilizer of the present invention is dissolved in a solvent such as cyclohexane, with a thermoplastic polymer solution such as a thermoplastic polymer solution after completion of polymerization of the polymer, and distilling the solvent off to obtain a thermoplastic polymer composition.

The stabilizer containing Compound (1) of the present invention impart thermal stability to the thermoplastic polymer. Herein, thermal stability of the thermoplastic polymer composition containing the stabilizer and the thermoplastic polymer can be assessed by heating the composition at 180° C. to melt it, measuring a yellowness index (YI) value using a chromatometer according to JIS K7105, subsequently, further heating the composition at 180° C. for 2 hours, measuring a YI value of the composition after heating, and evaluating thermal stability by a difference between the YI value of the composition after heating and the YI value of the composition before heating. As a difference between measured YI values is smaller, discoloration due to thermal deterioration is hardly caused, meaning that thermal stability is higher.

EXAMPLES

The following Examples and Comparative Examples illustrate the present invention in more detail, but it goes without saying that the present invention is not limited by Examples.

Example 1

<Production Example of Bisphenol>

2,4-di-tert-Pentylphenol (117.5 g), 0.9 g of p-toluenesulfonic acid monohydrate, and 6.9 g of a 78% aqueous sulfuric acid solution were mixed. To this was added dropwise a solution obtained by diluting 12.1 g of acetaldehyde with 28 g of xylene for 2 hours while retaining at 35 to 45° C. After addition, a temperature of the resulting solution was raised to 90° C., and the solution was retained at the same temperature for 3 hours.

After completion of temperature retaining, 157 g of xylene, 59 g of water and 11.7 g of a 25% aqueous sodium hydroxide solution were added, and the layers were separated to remove the aqueous layer. The resulting oily layer was washed with water, and subjected to azeotropic dehydration to remove water. After dehydration, 292 g of a pale yellow oil containing bisphenol represented by the formula (2) was obtained.

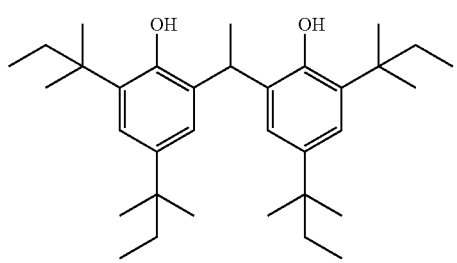
(2)

<Production Example of Bisphenol Monoester Compound>

To the pale yellow oil containing bisphenol was added 28 g of a 50% aqueous potassium hydroxide solution, a temperature of the solution was raised to 98° C., and the solution was retained at the same temperature for 3 hours. Thereafter, the solution was cooled to 50° C., hexane was added, and this was dehydrated under warming to a liquid temperature of 106° C., and cooled to 3° C. (this solution is designated A solution).

Another container was charged with 35.3 g of 2-carboxyethyl acrylate, and this was cooled to 1° C. under stirring. To this was added dropwise 26.7 g of thionyl chloride over 1.5 hours while retaining at 0 to 1° C. Thereafter, a temperature was retained at 1 to 17° C. for 3 hours, followed by degassing for 3 hours under reduced pressure (this solution is designated B solution).

To the A solution was added dropwise the B solution over 1 hour while retaining at 1 to 3° C., and a temperature was retained at the same temperature for 30 minutes. To this was added 150 ml of water, this was washed with water at 10 to 30° C., and the oily layer was obtained by layers separation. According to the same procedure, washing with water was repeated a total of three times. Thereby, 303 g of the brown oily layer was obtained.

When the resulting oily layer was analyzed by liquid chromatography, it was found out that 6.3% by weight of a compound represented by the formula (1-1)(hereinafter, referred to as Compound (1-1) in some cases) was contained in the composition except for the solvent.

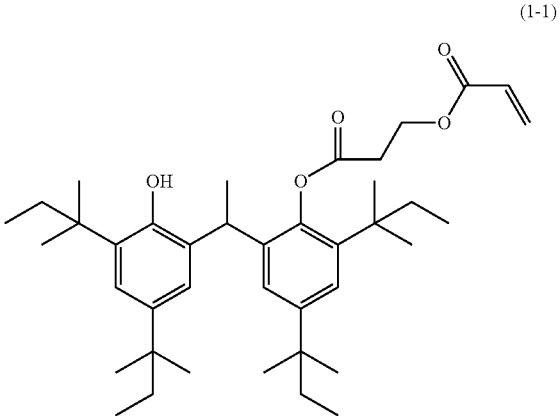
(1-1)

From the resulting oily layer, Compound (1-1) was isolated by a large scale collecting system (8A Type, manufactured by Shimadzu Corporation) using Sumipax ODS A-210 (diameter 20 mm×height 25 cm, diameter of filler: 5 μm) as a column.

Compound (1-1) was measured for $^1$H NMR spectrum using ECA-500 manufactured by JEOL and employing tetramethylsilane as an internal standard.

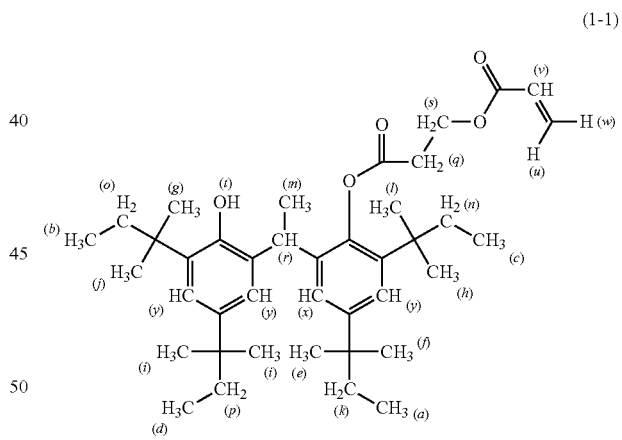
(1-1)

$^1$H NMR(500.16 MHz, CDCl$_3$) δ (ppm):0.49(3H, (a)), 0.55(3H, (b)), 0.66(3H,(c)), 0.70(3H,(d)), 1.01(3H,(e)), 1.03 (3H,(f)), 1.19-1.38(23H,(g)-(l)), 1.48(3H,(m)), 1.57-1.99 (7H,(n)-(p)), 3.09(2H,(q)), 3.89(1H,(r)), 4.61-4.64(2H,(s)), 5.55(1H,(t)), 5.72(1H, (u)), 6.04(1H, (v)), 6.36(1H, (w)), 6.49(1H, (x)), 7.12(3H,(y))

<Production Example of Thermoplastic Polymer Composition>

Compound (1-1) (11.6 mg) obtained in Example 1 was used at it was as the thermal stabilizer, and was dissolved in 5 ml of chloroform. To the resulting solution was added 2000 mg of a propylene-ethylene block copolymer (MI: 9-10 g/10 min) (230° C., 2.16 kg) (manufactured by SUMITOMO CHEMICAL COMPANY, LTD.) as the thermoplastic polymer, the mixture was stirred, and chloroform was spontaneously vaporized under 25° C. Further, the residue was heated and melted with a gear oven (GHPS-222, manufactured by Tabai Espec Corporation) at 180° C. for 1 hour to obtain a thermoplastic polymer composition.

<Thermal stability test>

The thermoplastic polymer composition obtained in Example 1 was measured for a yellowness index (YI) value (YI-1) using a chromatometer (CM-3500d, manufactured by Konika Minolta) according to JIS K7105, the composition was heated with a gear oven (GHPS-222, manufactured by Tabai Espec Corporation) at 180 ° C. for 2 hours, a YI value (YI-2) was measured again, and a difference between YI-2 and YI-1 was adopted as a discoloration degree, which was used to assess thermal stability of the thermoplastic polymer composition. As the discoloration degree is smaller, discoloration due to thermal degradation of the thermoplastic polymer composition is hardly caused, meaning that thermal stability is more excellent. The discoloration degree of the thermoplastic polymer composition of Example 1 was 10.03.

Letting the discoloration degree (13.15) of a thermoplastic polymer not containing the stabilizer (Comparative Example 1 described later) to be 100%, a ratio of an improved discoloration degree (ratio of reduced discoloration degree) was expressed as a discoloration degree improvement index. That is, since the discoloration degree improvement index of Example 1 is (13.15-10.03)/13.15 x 100 =23.7(%), improvement of 23.7% was seen in the thermoplastic polymer composition of Example 1 as compared with the thermoplastic polymer composition not containing the stabilizer.

Letting the discoloration degree (13.15) of a thermoplastic polymer not containing the stabilizer (Comparative Example 1 described later) to be 100%, a ratio of an improved discoloration degree (ratio of reduced discoloration degree) was expressed as a discoloration degree improvement index. That is, since the discoloration degree improvement index of Example 1 is (13.15–10.03)/13.15×100=23.7(%), improvement of 23.7% was seen in the thermoplastic polymer composition of Example 1 as compared with the thermoplastic polymer composition not containing the stabilizer.

Comparative Example 1

According to the same manner as that of <Production Example of thermoplastic polymer composition> except that Compound (1-1) obtained in Example 1 was not used, a thermoplastic polymer composition was obtained.

According to the same manner as that of Example 1 except that the resulting thermoplastic polymer composition was used, thermal stability of the thermoplastic polymer composition was assessed. Results together with those of Example 1 are shown in Table 1.

Comparative Example 2

According to the same manner as that of Example 2 except that 11.6 mg of 2,4-di-t-pentyl-6-[1-(3,5-di-t-pentyl-2-hydroxyphenyl)ethyl]phenyl acrylate (Sumilizer GS, manufactured by SUMITOMO CHEMICAL COMPANY, LTD.; hereinafter, referred to as Compound A in some cases) was used in place of Compound (1-1) obtained in Example 1, a thermoplastic polymer composition was obtained.

According to the same manner as that of Example 1 except that the resulting thermoplastic polymer composition was used, thermal stability of the thermoplastic polymer composition was assessed. Results together with those of Example 1 and Comparative Example 1 are shown in Table 1.

TABLE 1

| | Thermoplastic polymer (mg) | Stabilizer (mg) | | Discoloration degree (YI value) | Discoloration degree improvement index (%) |
| | | Compound (1-1) | Compound (A) | | |
|---|---|---|---|---|---|
| Example 1 | 2000 | 11.6 | — | 10.03 | 23.7 |
| Comparative Example 1 | 2000 | — | — | 13.15 | 0.0 |
| Comparative Example 2 | 2000 | — | 11.6 | 12.22 | 7.1 |

INDUSTRIAL APPLICABILITY

The compound of the present invention can further improve thermal stability of the thermoplastic polymer.

What is claimed is:

1. A bisphenol monoester compound represented by the formula (1-1):

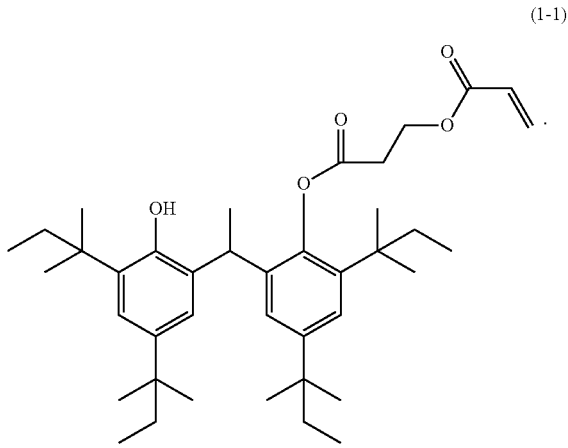

(1-1)

2. A stabilizer comprising the bisphenol monoester compound as defined in claim 1 as an active component.

3. The stabilizer according to claim 2, wherein the stabilizer contains the bisphenol monoester compound at 0.005 to 100% by weight.

4. A thermoplastic polymer composition comprising the stabilizer as defined in claim 2, and a polypropylene-based resin.

5. A process for producing the bisphenol monoester compound as defined in claim 1 comprising reacting bisphenol represented by the formula (2):

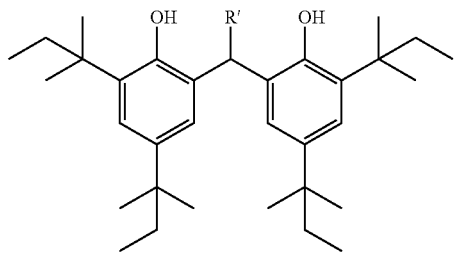

(2)

wherein R' represents a methyl group with a compound represented by the formula (3):

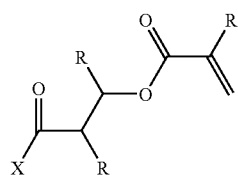

(3)

wherein each R represents a hydrogen atom, and X represents a halogen atom, a hydroxy group or an alkoxy group of a carbon number of 1 to 6.

6. A thermoplastic polymer composition comprising the stabilizer as defined in claim 3, and a polypropylene-based resin.

7. A method for thermally stabilizing a polypropylene-based resin, which comprises blending the polypropylene-based resin and the stabilizer of claim 2.

8. A method for thermally stabilizing a polypropylene-based resin, which comprises blending the polypropylene-based resin and the stabilizer of claim 3.

* * * * *